(12) United States Patent
Mehta

(10) Patent No.: US 8,166,579 B2
(45) Date of Patent: May 1, 2012

(54) POWER OPERATED URINAL APPARATUS FOR A COMMODE

(76) Inventor: Mahendra Nagindas Mehta, Fort Worth, TX (US)

( * ) Notice: Subject to any disclaimer, the term of this patent is extended or adjusted under 35 U.S.C. 154(b) by 313 days.

(21) Appl. No.: 12/544,913

(22) Filed: Aug. 20, 2009

(65) Prior Publication Data

US 2010/0223720 A1   Sep. 9, 2010

Related U.S. Application Data

(60) Provisional application No. 61/209,059, filed on Mar. 3, 2009, provisional application No. 61/176,668, filed on May 8, 2009, provisional application No. 61/182,040, filed on May 28, 2009.

(51) Int. Cl.
*A47K 11/02* (2006.01)

(52) U.S. Cl. ............................. 4/144.1; 4/342

(58) Field of Classification Search ...... 4/315, 340–342, 4/144.1–144.2, 144.4
See application file for complete search history.

(56) References Cited

U.S. PATENT DOCUMENTS

| | | | |
|---|---|---|---|
| 3,412,408 A | 11/1968 | Michal, Jr. | |
| 3,500,480 A * | 3/1970 | Michal, Jr. | ........................ 4/301 |
| 3,625,654 A * | 12/1971 | Van Duyne | .................. 600/574 |
| 3,822,419 A | 7/1974 | Wilson, Sr. | |
| 4,137,579 A | 2/1979 | Soler | |
| 4,180,875 A | 1/1980 | Wilson | |
| 4,285,076 A * | 8/1981 | Dickstein | ......................... 4/341 |
| 4,750,219 A | 6/1988 | Williams | |
| 4,881,660 A | 11/1989 | Suttles | |
| 4,920,171 A | 4/1990 | Hutton, Jr. et al. | |
| 4,985,940 A * | 1/1991 | Jones | ................................. 4/301 |
| 5,566,400 A | 10/1996 | Jonec | |
| 5,655,230 A | 8/1997 | Corbin | |
| 6,038,708 A | 3/2000 | Schreck | |
| 6,305,034 B1 | 10/2001 | Urrutia | |
| 6,361,784 B1 | 3/2002 | Brennan | |
| 6,408,449 B1 | 6/2002 | Aguirre | |
| 6,499,155 B1 | 12/2002 | Barrios | |
| 6,821,940 B2 | 11/2004 | Bullock | |
| 7,412,732 B1 | 8/2008 | Leonard | |
| 7,516,923 B2 | 4/2009 | Rossini | |

* cited by examiner

*Primary Examiner* — Charles Phillips

(57) ABSTRACT

The commode-urinal prevents urine-splatters around the commode, and stores extra toilet rolls and flushable funnels. In power-driven commode-urinal, a user activates a sensor; a jaw clamps a flushable funnel to an arm. The arm moves out of dispenser dispensing and suspending the funnel above the commode-bowl. The user urinates through the funnel, which channels urine into the bowl preventing urine-splatters around the commode. After urinating, the user activates the sensor; the jaw retracts releasing used funnel into the bowl. The arm retracts into the dispenser clearing the commode to function unimpeded. Flushing drains away the funnel. In manually-operated commode-urinal, when ready to urinate, the user pulls a funnel from the dispenser. Keeping bottom end of the funnel in middle of the bowl, the user urinates through it. After urinating, the user drops the funnel into the bowl and flushes. The funnels have wet strength, water repellency, but degrade in drains.

23 Claims, 10 Drawing Sheets

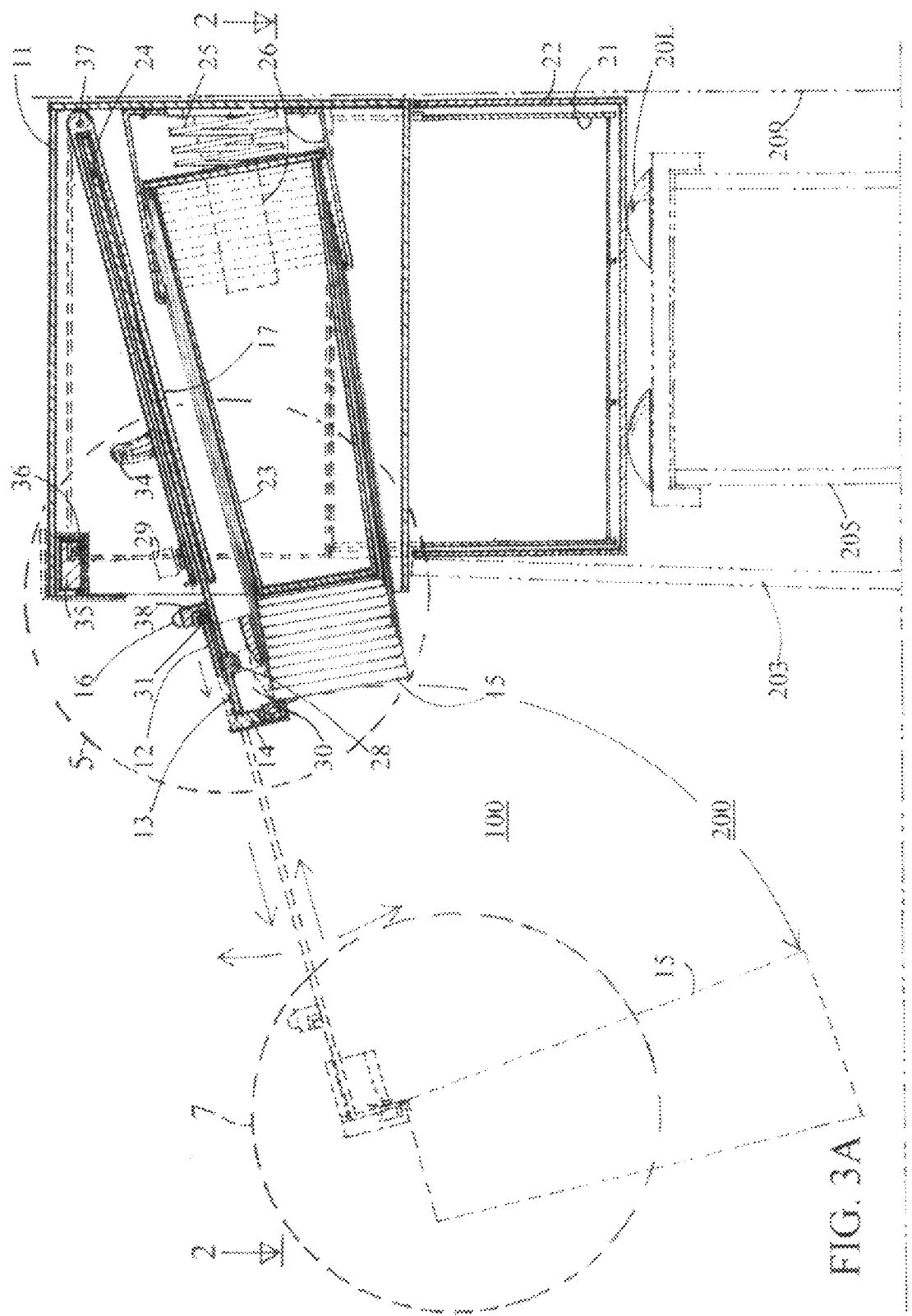

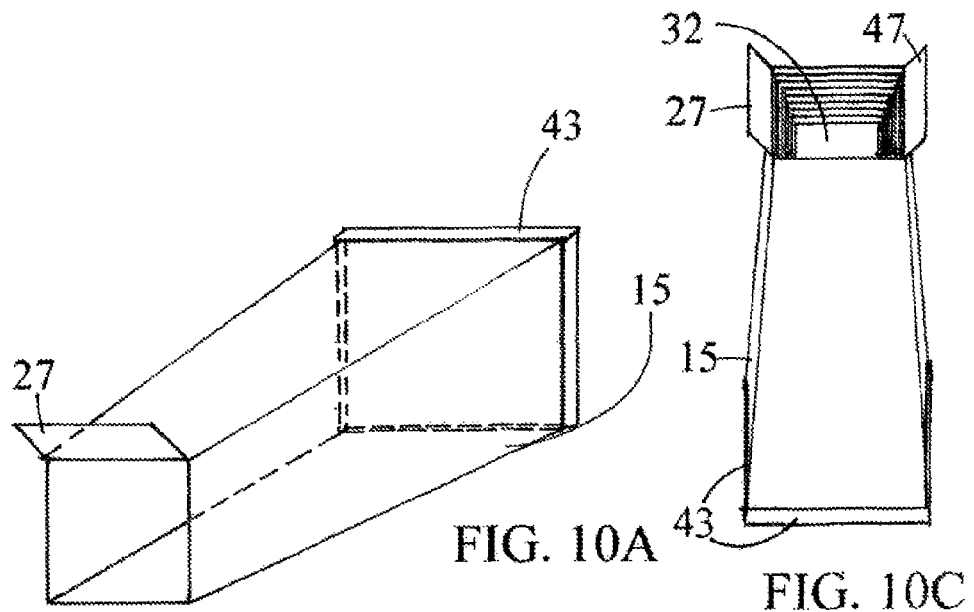
FIG. 10A
FIG. 10C
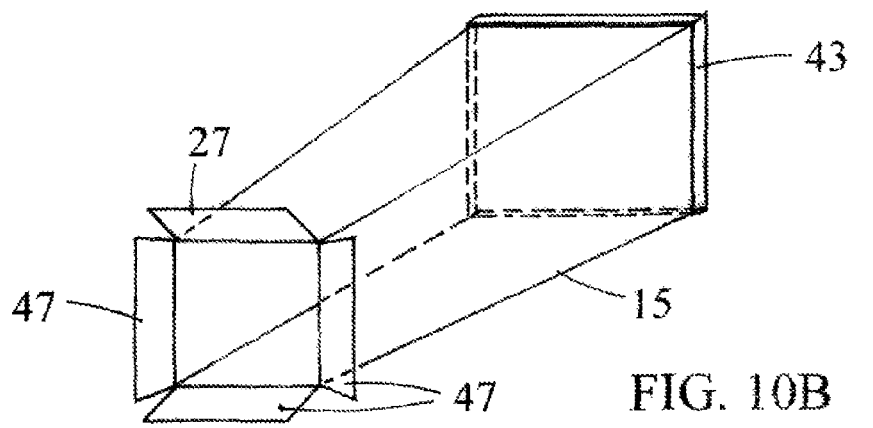
FIG. 10B
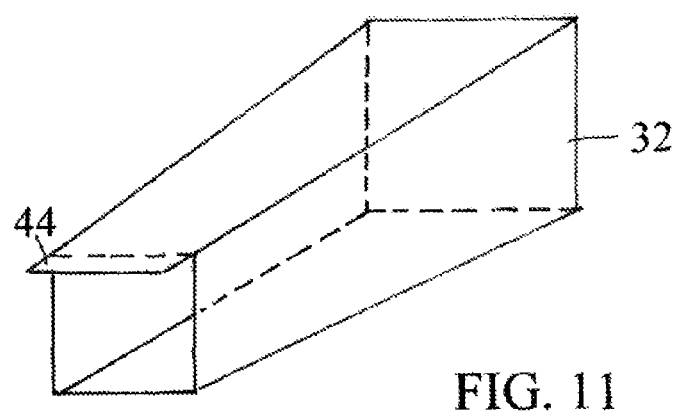
FIG. 11

POWER OPERATED URINAL APPARATUS FOR A COMMODE

CROSS-REFERENCE TO RELATED APPLICATIONS

This application claims the benefits of Provisional Patent Application Ser. No. 61/209,059, filed 2009 Mar. 3; 61/176,668, filed 2009 May 8; and 61/182,040, filed 2009 May 28 by the present inventor.

FEDERALLY SPONSORED RESEARCH

Not applicable

SEQUENCE LISTING

Not applicable.

BACKGROUND

1. Field of the Invention

This application relates to a power-operated urinal apparatus for a commode or a toilet and a urinal method, which directs urine through a funnel into a commode or toilet.

2. Prior Art

The usage of urinals is a known method to urinate in most public restrooms. However, most residences and many commercial places do not offer the convenience of urinals. Therefore, commodes or toilets designed to receive human waste from a sitting position are also used for urination from a standing position. Typically, users stand to urinate for comfort and to avoid germs on commode seats. In the process, however, urine spills on rim of the commode and floor around the commode or toilet, no matter how careful the users may be. Even traditional urinals do not prevent urine spills and consequently odor emanates from them. Urine splashing on water of the commode bowl also leads to a sound that may be embarrassing. Urine spills result in a non-hygienic condition and require additional cleaning around the commode. Furthermore, urine spills can stain a rug, if a rug has been placed near the commode. Some users, risking the spread of germs, raise both lids of the commode to an upright position to urinate into the commode. They seldom put them back, which is inconvenience to the next user. From this point ahead in this document, "commodes or toilets" will be referred to as "commodes."

Standard commodes and urinals are two separate fixtures requiring separate spaces, drains, and plumbing lines, which cost a lot more than a single fixture. Several attempts have been made in past to combine a urinal and a commode to provide an economical and space-saving solution. U.S. Pat. No. 6,408,449 issued to Aguirre (2002) disclosed a toilet assembly in combination with a urinal. However, this assembly can be very expensive, because it requires extra floor space and plumbing lines. Most existing toilets do not have the extra space required to add a urinal. In U.S. Pat. No. 5,655,230 issued to Corbin (1997), and in U.S. Pat. Nos. 3,412,408 and 3,500,480 issued to Michal (1968 and 1970 respectively), urinal attachments for toilet bowls are presented. Although these types of urinal attachments can be added to existing toilets, they will make the toilet space more crowded and unpleasant. These urinal attachments require skilled personnel to install the attachments resulting in extra expenses, time, efforts, and inconveniences. Other prior art devices include U.S. Pat. Nos. 3,822,419; 4,137,579; 4,180,875; and 4,750,219. Most of these prior art devices require significant modifications and plumbing changes and may be unappealing to users. U.S. Pat. No. 5,566,400 issued to Jonec (1996) disclosed a disposable flat-folded male urinary aid and compact portable dispenser. Before urinating, the male must use his hands to pull out the urinary aid from the portable dispenser, which may be unstable. Then he must unfold the long urinary aid, insert penis in larger top end and place smaller bottom end of the urinary aid into the toilet water. A lot of time is wasted doing all of these steps, even before urinating. During urination, the male must hold the urinary aid and then drop it into the toilet after use. U.S. Pat. No. 6,305,034 issued to Urrutia (2001) disclosed a wall attached extensible and retractable urine deflecting apparatus for use with a toilet. This apparatus also requires substantial use of human hands before, and after urinating. Before use, the male has to extend and after the use he has to retract the apparatus manually. Also, he has to manually lower a deflecting sheet substantially into the toilet bowl water; each use requires a substantial amount of the deflecting sheet. The deflecting sheet used in this apparatus can not reliably channel the urine flow into the toilet. Risk of urine spills still remains. Both of these prior art devices require substantial use of human hands and are unhygienic, inconvenient, and time consuming. Most of the prior art devices for urinary use of commodes have not solved the problem of urine spilling and splashing to any degree of satisfaction.

SUMMARY OF THE INVENTION

A power-operated urinal apparatus is to be used with a toilet, the toilet having an aperture for receiving human waste. The urinal apparatus comprises a supply of flushable funnels, with each flushable funnel having a top open end and a bottom open end, and a passage between the two ends, and a power-driven dispenser. The power-driven dispenser activated by a user, the dispenser being movable under power from a stored position where the dispenser allows unimpeded use of the aperture, and an extended position where the dispenser locates and holds one of the flushable funnels in a suspended position with the top end of the flushable funnel above the aperture and the bottom end of the flushable funnel located relative to the aperture to direct fluids from the flushable funnel into the aperture without requiring any contact between the user and the apparatus during the use of the apparatus. The power-driven dispenser further being operable to move the power-driven dispenser under power to cause the dispenser to release the flushable funnel into the toilet and to move the dispenser from the extended position to the stored position, without requiring any contact between the user and the apparatus at any time during use of the apparatus.

The flushable funnels in the supply of flushable funnels are at a first orientation and the flushable funnel in the suspended position is at a second orientation that is different from the first orientation. The flushable funnels are made of water-flushable materials tough enough to withstand fluids, slightly slippery, and have transitory water repellency. The power-driven dispenser further comprises a power-driven movable arm. The movable arm is supported by a sleeve for enabling the movable arm to move between the stored position and the extended position. The sleeve is pivotally supported with the aid of a track device for enabling the sleeve to move up and down. There is also means for holding the sleeve up to facilitate reloading a plurality of the flushable funnels to the supply of flushable funnels. The movable arm includes a means for height adjusting for a user to adjust a height of the top of the flushable funnel in the suspended position suitable to the user. The movable arm is moved between the stored position and the extended position by a rack and pinion device. The rack and pinion device is connected to a first motor. An end plate and a stop are provided on the movable arm. A movable jaw moves on the movable arm between the end plate and the stop. The end plate and the jaw releasably clamp a portion of one of the funnels.

A sensor is activated by a human user of the aperture. The sensor initiates the operation of a second motor that moves the jaw to a clamping position with the end plate before the first motor is initiated to extend the movable arm to the extended position. The supply of flushable funnels comprises a nested arrangement. Each of the flushable funnels includes a tail portion at the top end to be clamped. The sensor activation is a first activation. The sensor has a second activation by a human user when the movable arm is in the extended position. By second activation the sensor initiates the operation of the second motor that moves the jaw out of the clamping position and allows the flushable funnel in the suspended position to drop into the aperture. When the second activation of the sensors occurs and after the second motor moves the jaw out of the clamping position, the first motor moves the movable arm to the stored position. The supply of flushable funnels comprises a nested arrangement, with each flushable funnel is tapered from the top end to the bottom end. The power-driven dispenser comprises a movable arm. The supply of flushable funnels includes a biasing device to urge the flushable funnels towards an end of the movable arm.

The supply of flushable funnels includes a hub to support a plurality of flushable funnels. The supply of flushable funnels includes restraining arms with a portion extending inwards. A protrusion is adjacent to the bottom end of the flushable funnel to cooperate with the restraining arms to dispense the flushable funnels from the nested arrangement one at a time. The flushable funnel includes a flap portion around at least a portion of the top end forming a handle. The apparatus includes storage space to store extra supplies of the flushable funnels. The apparatus includes storage space to store toilet paper. The apparatus can be made in separate sections adapted to reduce its packing size. The toilet aperture receives human waste. At least one means for fastening on an exterior of the urinal apparatus mounts the urinal apparatus to an object. The toilet has a water tank. The urinal apparatus is attached to the water tank or attached close to the toilet.

A method of assisting a standing human in urinating into a toilet designed for receiving human waste comprises the steps of providing a supply of flushable funnels, and providing a power-driven dispenser. The power-driven dispenser removing a flushable funnel from the supply of flushable funnels and by means of the power-driven dispenser, suspending the flushable funnel above the toilet to provide a path for fluids into the toilet without requiring any contact between the user and the flushable funnel during use of the flushable funnel. By means of the power-driven dispenser, releasing the suspended flushable funnel and allowing the flushable funnel to fall into the toilet without requiring any contact between the user and the flushable funnel at any time during use of the apparatus. The method further comprises the step of causing the power-driven dispenser to move the power-driven dispenser from the extended position to the stored position. The method further comprises the step of flushing the toilet to flush away the fluids and the dropped flushable funnel. The flushable funnel is suspended by way of a tail. The flushable funnel is suspended above the toilet by deploying a power-driven movable arm. The movable arm is returned to a stored position leaving the aperture to function unimpeded.

A urinal device comprises a flushable sleeve having two ends, one of the ends being larger than the other, with each end being open, and a passage between the two ends. A flap is adjacent to the smaller end and forms a handle. The flushable sleeves are made of flushable cellulosic waterleaf with minimal amount of wet strength resin from a group of melamine formaldehyde, urea formaldehyde or neutral cure wet strength, said waterleaf coated to at least one surface with a composition of 20% by weight to 70% by weight of relatively large particle size delaminated clay, with the balance being a polyethylene based resin composition produced by drying of a colloidal polyethylene in water composition together with said clay; whereby the resultant surface coating provides surface water repellency without impairing the ability of the waterleaf sleeve to be disposed of by flushing. The sleeve is part of a nested stack of sleeves.

The object of this embodiment is to provide a simpler, economical, and hygienic urinal apparatus for a commode to prevent urine spills on the rim of and floor around the commode. The apparatus does not require any additional plumbing or floor space and can be installed by a lay person within a short time.

BRIEF DESCRIPTION OF DRAWINGS

In the drawings, like reference numbers among different embodiments indicate like parts or components. Closely related figures have the same numbers but different alphabetic suffixes.

FIGS. 3A and 3B show a side cross-sectional view of the preferred embodiment, indicated by section lines 1-1 in FIG. 2, with FIG. 3A showing the urinal apparatus and FIG. 3B showing a commode.

FIG. 10A shows a perspective view of the preferred embodiment of flushable funnel.

FIG. 10B shows a perspective view of the second preferred embodiment of the flushable funnel with fin portions added.

FIG. 10C shows the flushable funnels placed around a cardboard core in a nested arrangement.

FIG. 11 shows a perspective view of the cardboard core.

Figure 1:
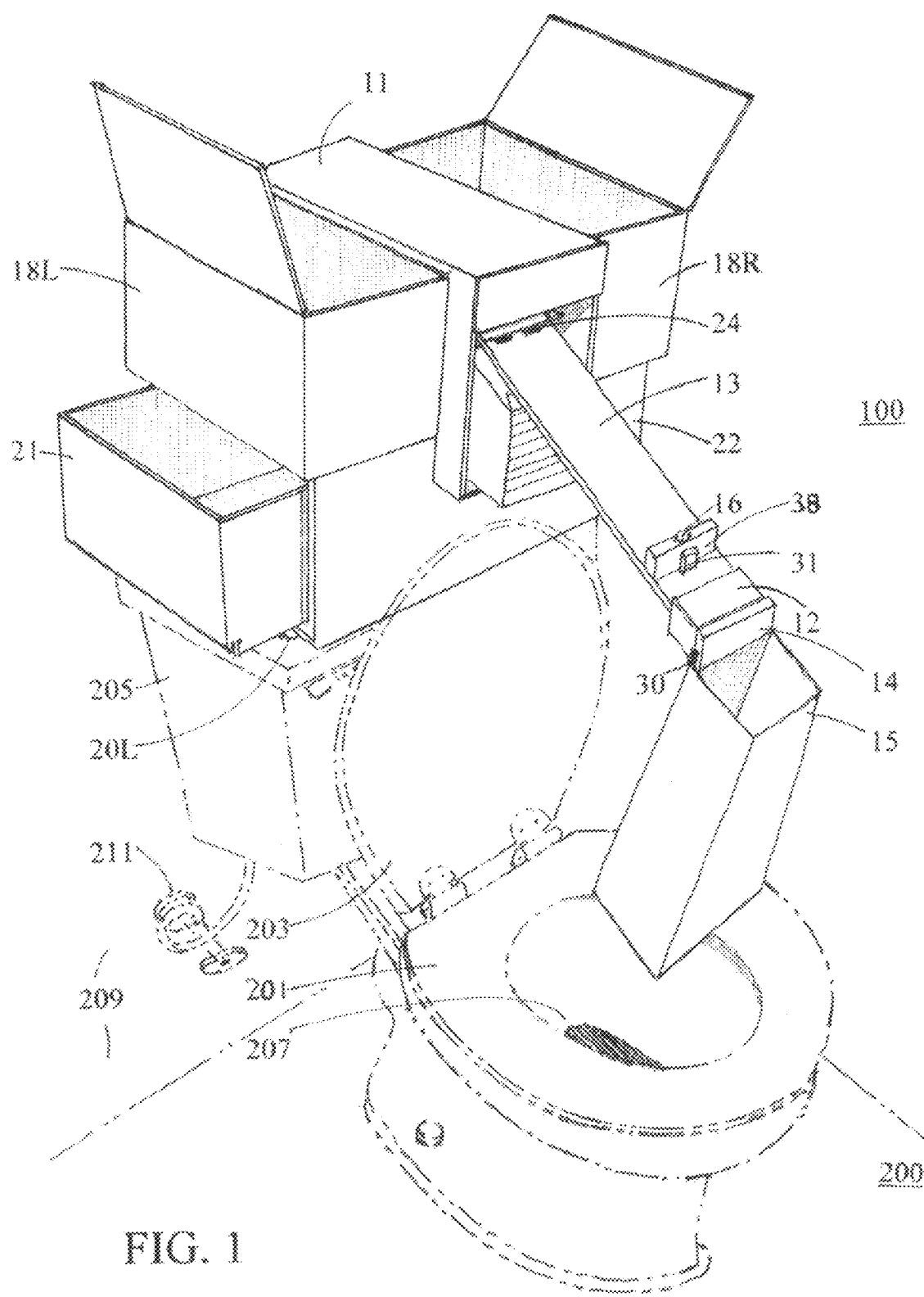
FIG. 1 is a perspective view of the preferred embodiment showing a dispensed and suspended flushable funnel ready for use.

| | DRAWINGS-Reference Numerals | | |
|---|---|---|---|
| 100 | power-operated urinal apparatus | 200 | commode |
| 11 | power-driven dispenser | 201 | commode seat |
| 12 | jaw | 203 | commode cover |
| 13 | movable arm | 205 | water tank |
| 14 | end plate | 207 | commode bowl |
| 15 | flushable funnel | 209 | wall |
| 16 | activation device or sensor | 211 | water supply |
| 17 | sleeve | 213 | drain or sewage line |
| 18L | container | 18R | container |
| 20L | fastening device | 20R | fastening device |
| 21 | drawer | 22 | storage section |
| 23 | hub | 24 | height adjusting device |
| 25 | biasing device | 26 | restraining arms |
| 27 | tail portion | 28 | reversible motor |
| 29 | reversible motor | 30 | switch |
| 31 | switch | 32 | core |
| 33 | groove | 34 | track |
| 35 | battery | 36 | electric plug |
| 37 | pivot | 38 | stop |
| 39 | projection | 40 | tongue |
| 41 | channel | 42 | lid |
| 43 | protrusion | 44 | flange |
| 45 | ball | 46 | socket |
| 47 | fin portion | 48 | notch |
| 49 | band | 50 | sear |
| 51 | rack | 52 | pinion |

DETAILED DESCRIPTION OF EMBODIMENTS

FIGS. 1, 2, 3A-3B and 10A

The invention may be best described by reference to the drawings. One preferred embodiment of the power-operated urinal apparatus 100 for a commode 200 is illustrated in various views: FIG. 1 (perspective view), FIG. 2 (top view), FIGS. 3A and 3B (side cross-sectional view), and FIG. 10A (flushable funnel). Part number follows name of the part. The apparatus 100 is attached on water tank 205 of the commode 200 by fastening devices 20L and 20R, which can be suction cups or other suitable fastening devices. The fastening devices are built under a storage section 22, but can be built anywhere on the apparatus 100. The fastening devices secure the apparatus on top of the water tank or on a wall near the commode. This position allows the commode to function unimpeded. A power-driven dispenser 11 is attached to the storage section 22, which has a drawer 21 and can store extra flushable funnels 15. The dispenser 11 has a truncated cone shaped hub 23 to support the flushable funnels 15 in nested arrangement. The funnels 15 are ready to be dispensed one at a time. A movable arm 13 is provided in the dispenser 11 to extend, and suspend a funnel 15 above the commode bowl 207 when activated by a user. This extended position converts the commode into a temporary urinal without requiring any contact between the user and the apparatus.

A plurality of restraining arms 26 having a portion extending inwards to support the hub 23. The restraining arms 26 are flexible enough to release one funnel 15 at a time with cooperation of a biasing device 25. The biasing device 25 is located between the rear wall of the dispenser 11, and the hub 23. The restraining arms 26 are anchored to the dispenser 11. The biasing device 25 pushes the hub 23 outward when the outer most funnel 15 is pulled out of the nested stack of funnels 15. This push is just enough to automatically place the newly exposed tail portion 27 of the next outer most funnel 15 close to an end plate 14 located on outer end of the movable arm 13. The positioning of the tail portion 27 keeps the outer most funnel 15 ready to be clamped by a jaw 12 against the end plate 14. The movable arm 13 is supported by a sleeve 17 for enabling the arm 13 to move between the stored position and the extended position when activated. The movable arm 13 also has a height adjusting device 24, which may be a constant torque friction hinge or other suitable device. The device 24 helps a user to adjust the height of top end of the funnel in suspended position suitable to the user.

The movable arm 13 is moved between the stored and extended positions by a suitable rack and pinion device connected to a reversible motor 29. The motor 29 is connected to a battery 35 and an electric plug 36 for choice of a power supply. A switch 30 is provided on the end plate 14 to activate forward movement of the movable arm 13. A stop 38 is provided on the movable arm 13. A switch 31 is provided on the stop 38 to activate reverse movement of the movable arm 13. A suitable rack and pinion device is connected to a reversible motor 28 that moves the jaw 12 between the end plate 14 and the stop 38. The motor 28 is connected to the battery 35 and the electric plug 36 for choice of a power supply. An activation device 16 is provided, which can be a touchless sensor or a switch. The sensor 16 is placed on the stop 38 but can be placed anywhere on the apparatus 100. The first user activation of the sensor 16 is to move the arm 13 from the stored position to the extended position to suspend and hold a funnel 15. The second user activation of the sensor 16 is to drop the funnel and return the arm 13 from the extended position to the stored position. The apparatus has lidded containers 18L and 18R on either side of the dispenser 11, which can store extra toilet paper rolls.

In operation, upon first activation by a user, the sensor 16 initiates the operation of the motor 28 that moves the jaw 12 forward thereby clamping the tail portion 27 of the outer most funnel 15 with the end plate 14. Simultaneously, the jaw 12 activates the switch 30 and stops. This activation initiates operation of the motor 29 that extends the movable arm 13 to the extended position. While extending out, the arm 13 pulls out the clamped outer most funnel 15 from the nested stack of the funnels 15 loaded on the hub 23. Once the funnel 15 is pulled out completely from the stack (when the larger rear end of the funnel pulled out of the stack), the funnel 15 swings from the near horizontal orientation (shown in solid lines in FIG. 3A) to a near vertical orientation (shown in dashed lines in FIG. 3A) due to gravity. This suspended funnel above the commode directs fluids from the user into the commode. This operation does not require any contact between the user and the apparatus during use of the apparatus. The motor 29 stops when the movable arm 13 is fully deployed. The funnel 15 can help to reduce embarrassing sounds due to the urine stream hitting the inner sides of the funnel 15 instead of the water in the commode bowl. The user can adjust height of the top end of the funnel 15 by moving the deployed arm 13 up or down, as needed.

When the movable arm is in the extended position, and the user has finished urinating, the user activates the sensor 16. Upon this second activation, the sensor 16 initiates the operation of the motor 28 that moves the jaw out of the clamping position allowing the funnel 15 in the suspended position to drop into the commode bowl 207. Immediately following, the jaw 12 activates the switch 31 initiating the operation of the motor 29. This motor 29 moves the arm 13 to the stored position leaving the commode 200 to function unimpeded. The jaw 12 on the arm 13 clears the tail portion 27 and allows it to lift up. The jaw 12 has a tapered thin leading edge to move under the tail portion 27. Upon flushing, the dropped biodegradable funnel 15 flushes away with the urine and degrades in the sewage line. The first and second activations by the user can be done without touch, such as by waving a hand near or above the sensor 16. On the next activation, the operation repeats.

FIG. 1 is a perspective view of the urinal apparatus 100 placed on the water tank 205 of the commode 200. The movable arm 13 is extended by the power-driven dispenser 11 suspending a funnel 15 over the commode bowl 207; it is now ready for use. This is the temporary conversion of the commode 200 to a urinal. The jaw 12 is holding a suspended funnel 15 against the end plate 14. The dispenser 11 is placed on the storage section 22. The drawer 21 is drawn slightly open to show that it can store extra funnels 15. Containers 18L and 18R are drawn open to show that they can store toilet paper rolls. The sensor 16 is placed on the stop 38 but it can be placed anywhere on the apparatus. First activation of the sensor 16 moves the jaw 12 forward clamping the funnel 15 and activating the switch 30. This activation extends the arm 13 forward and suspends the funnel 15. Second activation of the sensor 16 moves the jaw backward dropping the funnel 15 and activating the switch 31. This activation returns the arm 13 into the apparatus. The full operation is discussed previously, and in FIG. 3A, FIG. 5, and FIG. 7.

In phantom lines, FIG. 1 illustrates the commode 200, which includes commode seat 201, commode cover 203, water tank 205, and commode bowl 207. The commode may be positioned against a wall 209 and is connected to a water supply 211 and a drain line 213 (see FIG. 3B).

FIG. 1 further shows the urinal apparatus 100 includes the fastening devices 20L and 20R (only one 20L is visible in FIG. 1), which attach the apparatus 100 to the water tank 205. Additionally, the storage section 22 can be placed so that the drawer 21 can open from the left side or from right side; it can also be opened from the front or can be designed with a lids on any side. The dispenser 11, the storage section 22 including the drawer 21, the containers 18L and 18R, can be made from rigid or semi-rigid plastic or other suitable materials.

FIG. 1 further shows the movable arm 13 has the height adjusting device 24 such as a constant torque friction hinge. The device 24 allows the user to position the height of the top end of the funnel 15 over the toilet to a suitable height; the device 24 holds the position until second activation of the sensor 16 moves the arm 13 back into the dispenser 11. Several constant torque friction hinges are available in the market, such as Reell's patented hinge.

Figure 2:
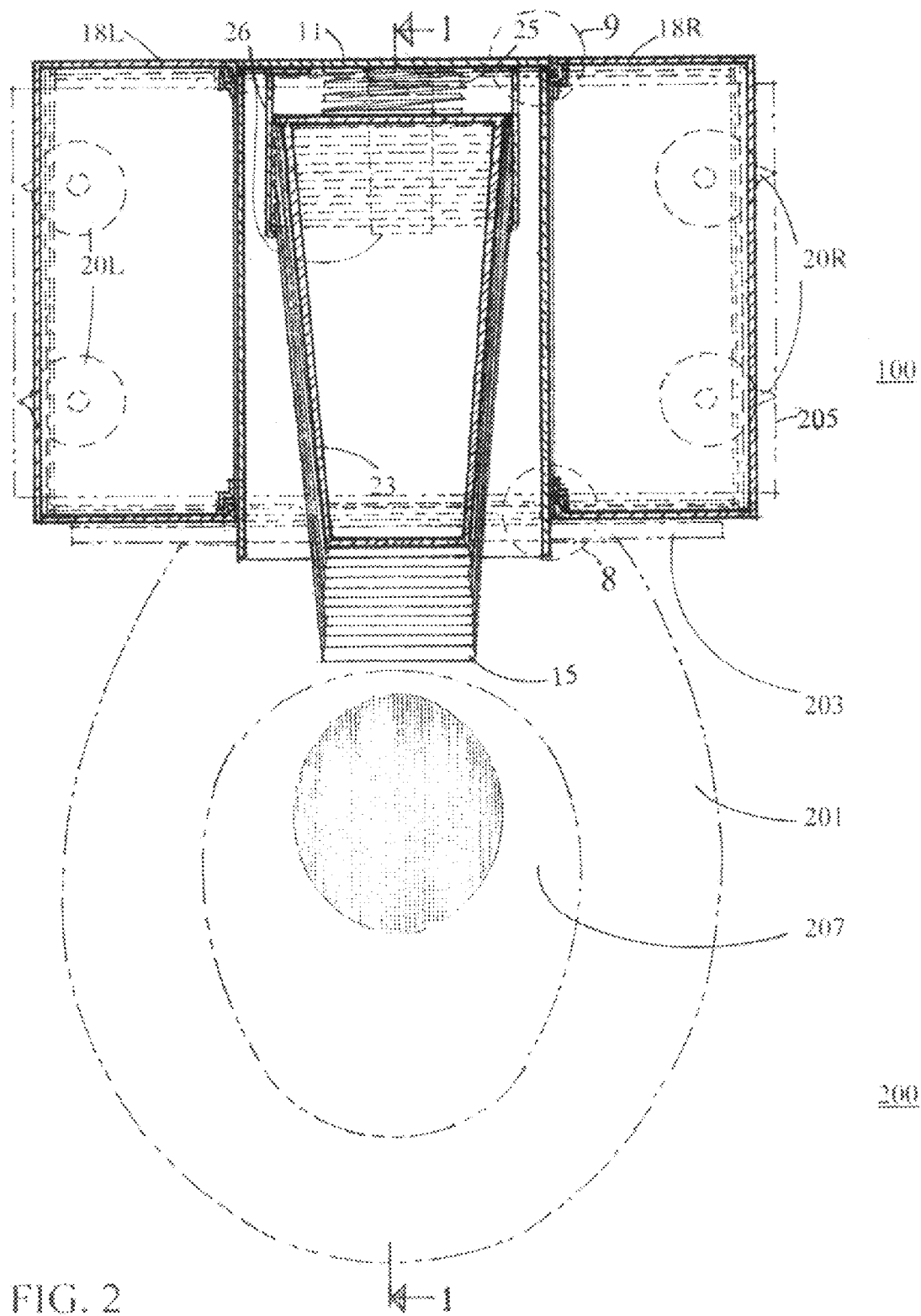
FIG. 2 is a top cross-sectional view of the preferred embodiment, indicated by section lines 2-2 in FIG. 3A.
Figure 8:
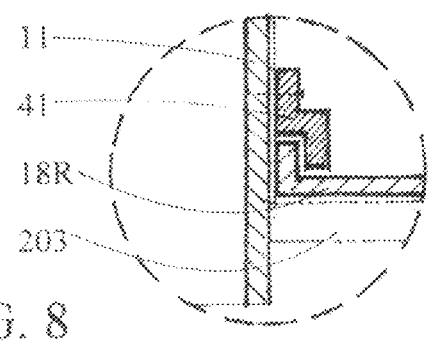
FIG. 8 shows details of the front joint between the container and the power-driven dispenser, indicated by the dashed circle 8 in FIG. 2.
Figure 9:
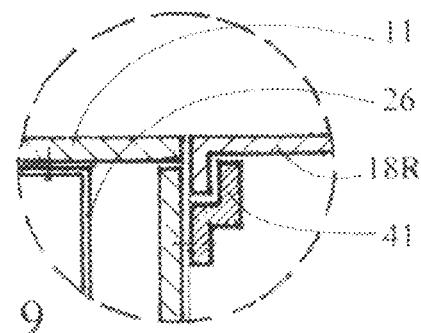
FIG. 9 shows details of the rear joint between the container and the power-driven dispenser, indicated by the dashed circle 9 in FIG. 2.

FIG. 2 is a top cross-sectional view of the urinal apparatus 100 showing the dispenser 11 including the hub 23. The containers 18L and 18R can store toilet paper rolls or other items. The restraining arms 26 are anchored to the dispenser 11. Along with the hub 23, the restraining arms 26 supports a plurality of funnels 15 placed on the hub 23. The biasing device 25 pushes the hub 23 outwards. The movable arm 13 (not shown on FIG. 2), with cooperation of the restraining arms 26, dispenses a funnels 15 one at a time. The restraining arms 26 can have a portion extend inwards to hold the protrusions 43 (not shown on FIG. 2) of the funnels 15. The arms 26 are flexible enough to release the funnels 15 one at a time. Details at dashed circle 8 and 9 are shown in FIGS. 8 and 9, respectively.

In phantom lines, FIG. 2 shows the commode seat 201 in seating position, the commode cover 203 in upright position, the water tank 205 below the apparatus 100, and the commode bowl 207 of the commode 200.

In dashed lines, FIG. 2 show fastening devices 20L and 20R, which can be made of flexible plastic suction cups or other appropriate fastening device. The fastening devices 20L and 20R are built below the apparatus 100 and are sized to fit on and secure to the water tank 205. The apparatus 100 can be made attachable to the water tank or an object including a wall by way of suitable fastening device.

Figure 3B:
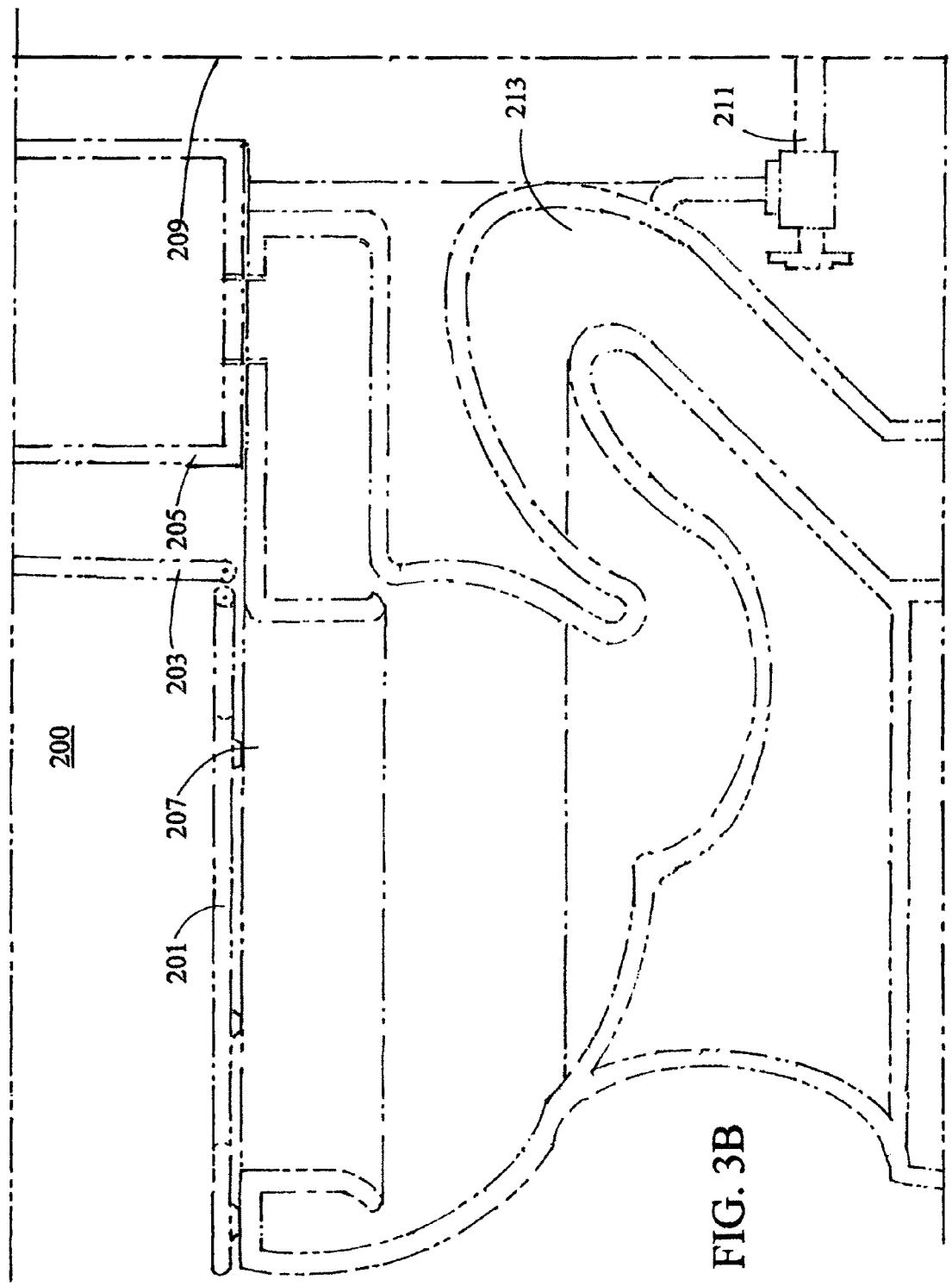

FIG. 3A and FIG. 3B show a side cross-sectional view of the urinal apparatus 100 for a commode 200. In solid lines, FIG. 3A shows the apparatus 100 storing a plurality of funnels 15 in nested arrangement around the hub 23 and a funnel 15 has not been dispensed. The movable arm 13 is in the stored position (shown in solid lines). Upon first activation by a user, the sensor 16 initiates the operation of the motor 28 that moves the jaw 12 forward thereby clamping the tail portion 27 of the outer most funnel 15 with the end plate 14. Simultaneously, the jaw 12 activates the switch 30, which initiates the operation of the motor 29 to extend the movable arm 13 to the extended position (shown in dashed lines). While extending out, the arm 13 pulls out the clamped funnel 15 from a nested stack on the hub 23. Once the funnel 15 is pulled out completely from the stack (when the larger rear end of the funnel is pulled out of the stack), the funnel 15 swings from the near horizontal orientation (shown in solid lines in FIG. 3A) to a near vertical orientation (shown in dashed lines in FIG. 3A) due to gravity. The lower end of the funnel 15 positions itself over the bowl 207 such that the urine flows into the bowl 207. The user urinates though the funnel 15. During pull of the funnel 15, the biasing device 25 pushes the hub 23 forward. This positions the next outer most funnel 15 and its tail portion 27 close to the end plate 14, ready for next user.

Figure 5:
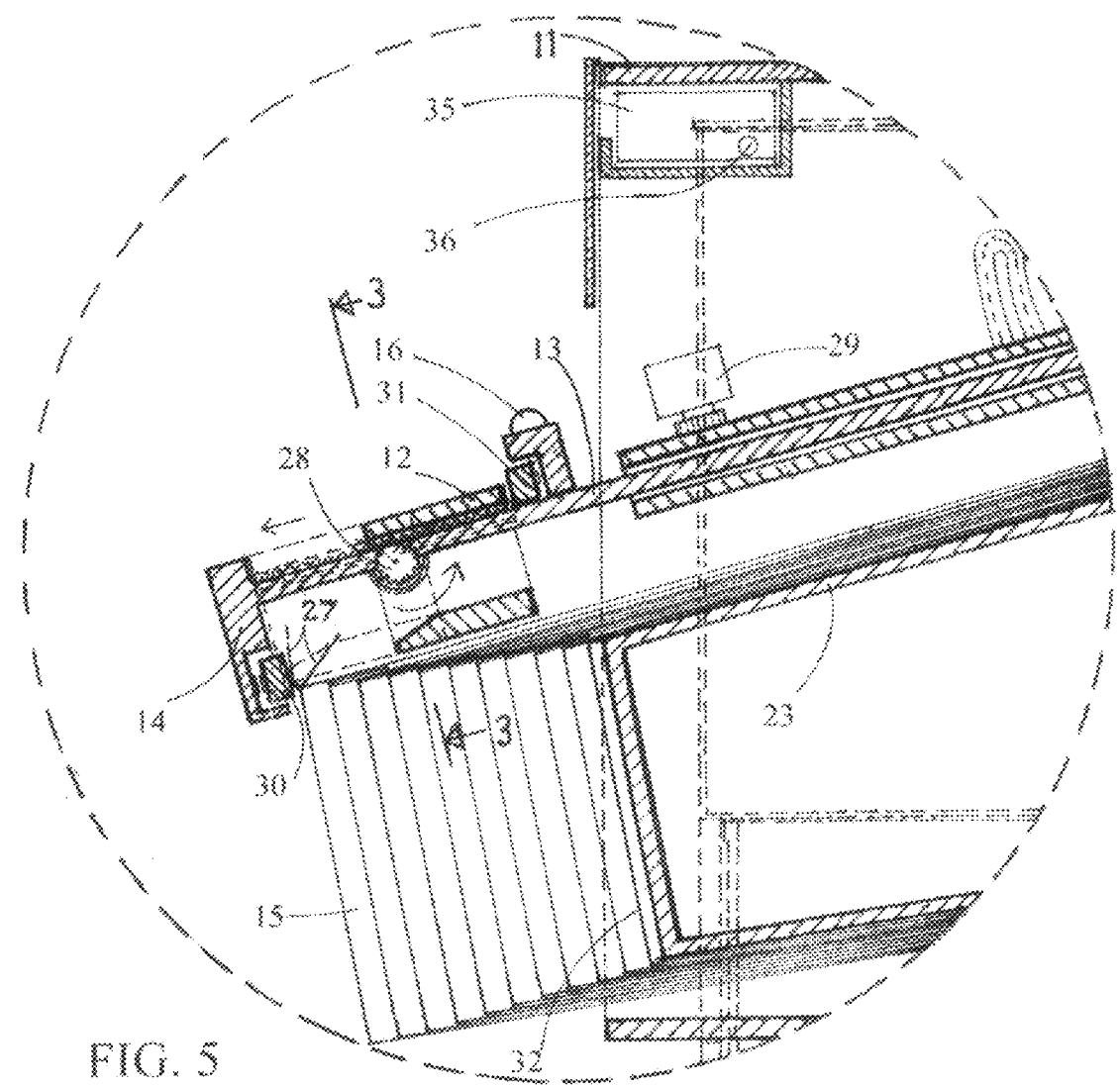
FIG. 5 shows a partial enlarged view of the operation from the stored-hub position, indicated by the dashed circle 5 in FIG. 3A.
Figure 7:
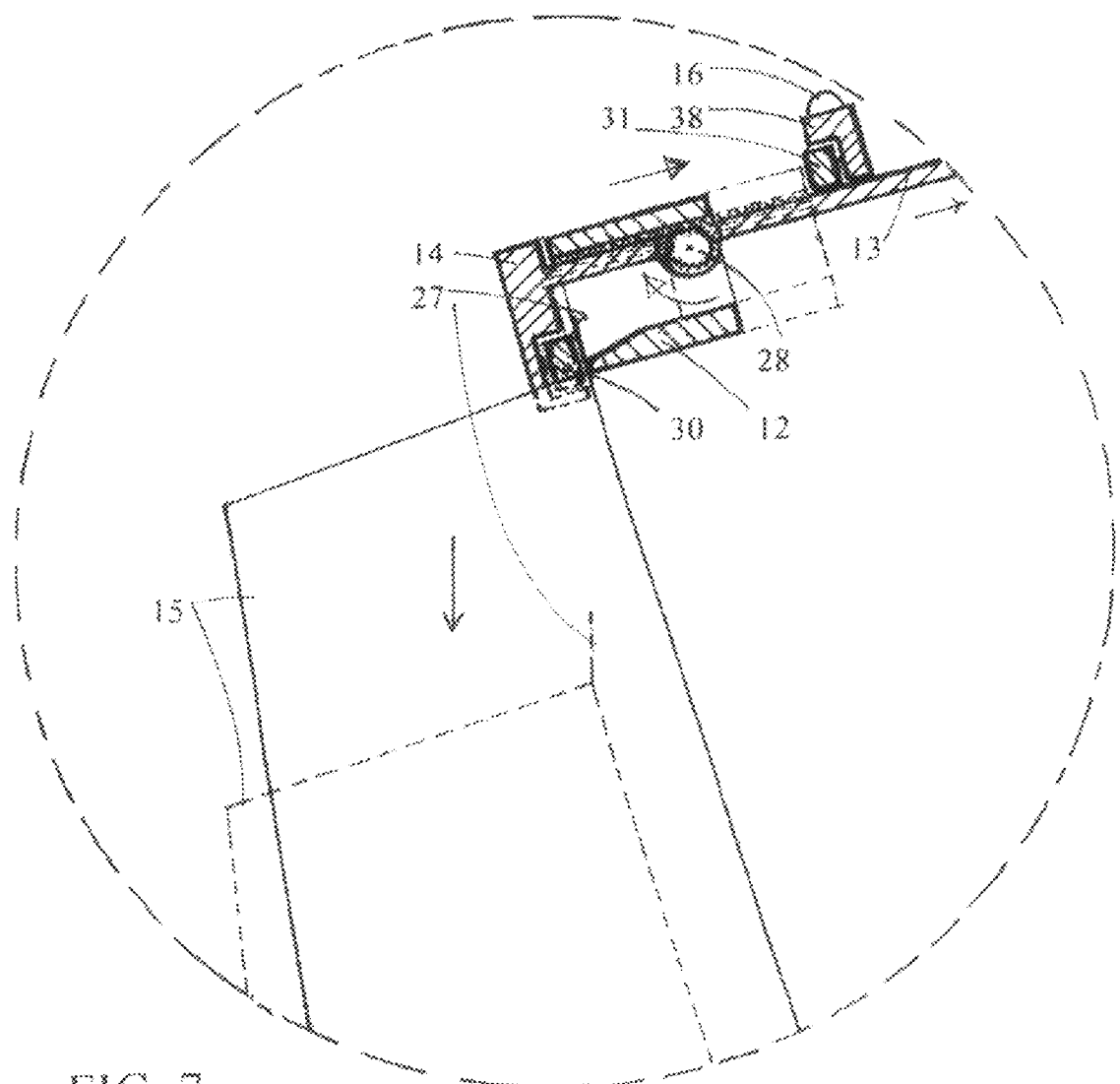
FIG. 7 shows a partial enlarged view of the operation from the dispensed and suspended position, indicated by the dashed circle 7 in FIG. 3A.

When the movable arm is in the extended position (shown in dashed lines), the user activates the sensor 16. This second activation initiates the operation of the motor 28 that moves the jaw 12 out of the clamping position. This allows the suspended funnel 15 to drop into the commode bowl 207. Immediately following, the jaw 12 activates the switch 31 initiating the operation of the motor 29, which then moves the arm 13 to the stored position. This stored position keeps the commode to function unimpeded. On the next first and second activation, the respective operation repeats. A sleeve 17, which can be a plate, a cylinder or other suitable device, supports the movable arm 13. A pivot 37 and tracks 34 attached on both sides of the dispenser 11 support the sleeve 17. The apparatus 100 is attached by fastening devices 20L, and 20R (not shown in FIG. 3A). The storage section 22 may include a drawer 21 to store extra funnels 15. The movable arm 13 has the height adjusting device 24 for the users to adjust the height of top of the funnel 15 at a suitable height. The motor 28 and 29 can be operated by the battery 35 or the electric plug 36. The details of the operation at dashed circles 5 and 7 are shown in FIGS. 5 and 7, respectively.

In phantom lines, FIG. 3A shows the top part of the commode 200, which can be positioned adjacent to a wall 209. The apparatus 100 can be placed on the water tank 205 (showed in partial view). The water tank is for flushing the commode 200. The commode cover 203, in upright position, appears in partial view.

In phantom lines, FIG. 3B shows the commode 200, which can be used in conjunction with the urinal apparatus 100 (shown in FIG. 3A) to convert the commode into a urinal. The commode 200 includes the commode seat 201, the commode cover 203, the water tank 205, and the commode bowl 207. The commode may be positioned against the wall 209. Water supply 211 supplies water to the water tank 205. The commode is connected to the drain 213.

Figure 4:
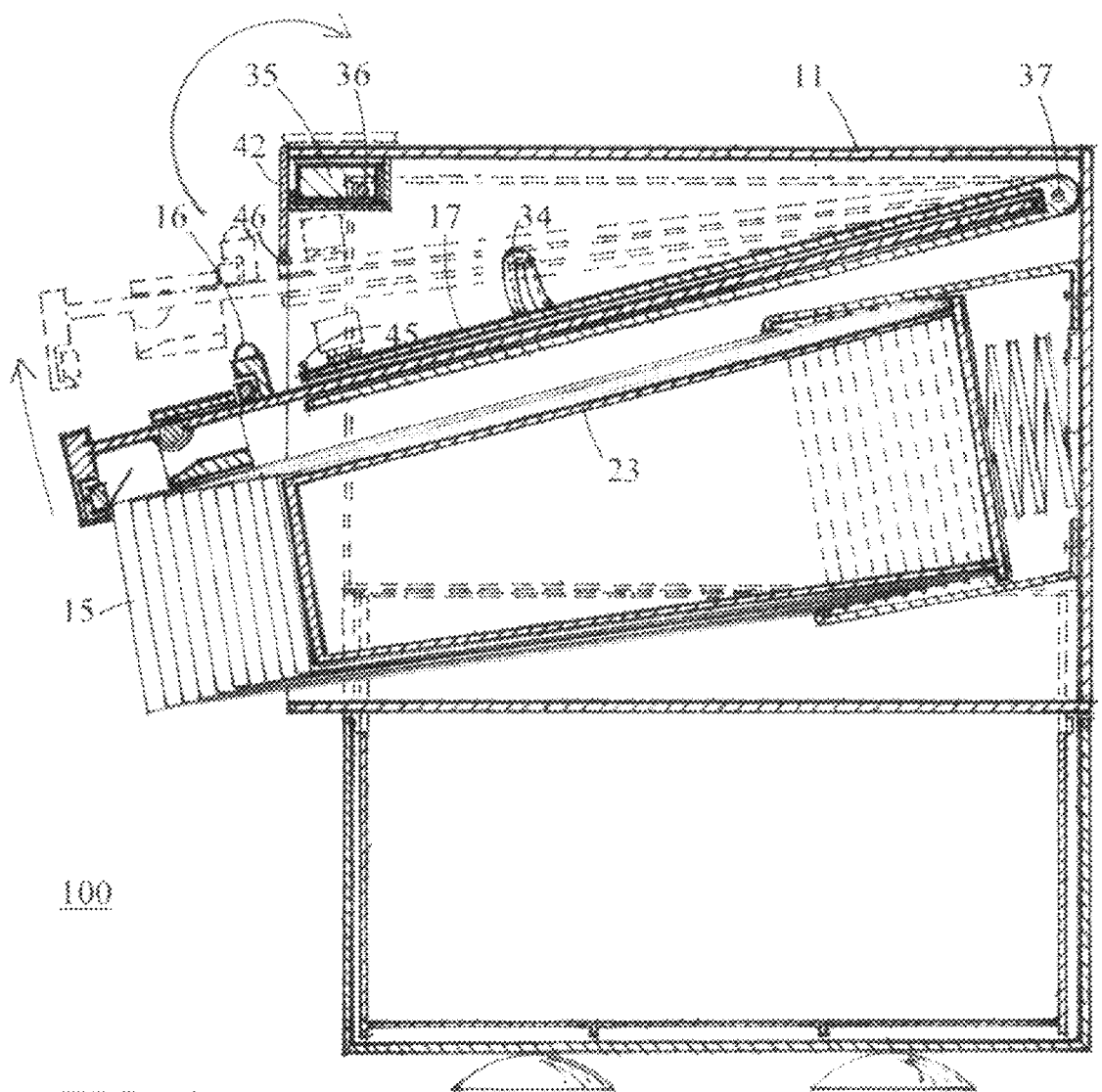
FIG. 4 is an enlarged side cross-sectional view of the preferred embodiment showing accessibility to the power-driven dispenser for restocking the funnels.

FIG. 4 is an enlarged side cross-sectional view of the urinal apparatus 100. The sleeve 17 can be moved upward and then reverted back to its original position with aid of the pivot 37 and the tracks 34. A ball 45 mounted on the sleeve 17 snaps into a socket 46 mounted on a lid 42 to hold the sleeve 17 in upward position, as needed. This feature allows a wider front opening of the dispenser 11 to restock a plurality funnels 15 on the hub 23, as needed. Different methods can be used for this purpose. The hub 23 is storing a plurality of funnels 15 in nested arrangement. A user activation of the sensor 16 activates the apparatus 100 to convert a commode in to a temporary urinal.

FIG. 4 further shows the lid 42 that may be opened to install the battery 35, which can be regular or rechargeable. Several regular or rechargeable batteries are available in the market. Optionally, the electric plug 36 can be used to plug into an electrical wall outlet for direct electric power supply to the apparatus 100.

FIG. 5 shows a partial enlarged view of the apparatus at dashed circle 5 in FIG. 3A. The funnels 15 are stacked in a nested arrangement around a core 32. The core 32 facilitates insertion of the funnels 15 on the hub 23. The reversible motor 28 and the jaw 12 are connected through a rack and pinion device. The motor 28 is attached to the pinion. The jaw 12 is attached to the rack. The reversible motor 29 and the movable arm 13 are connected through a rack and pinion device. The motor 29 is attached to the pinion. The movable arm 13 is attached to the rack.

FIG. 5 further shows that the funnel 15 has not been dispensed. The movable arm 13 is in the stored position. Upon first activation by a user, the sensor 16 initiates the operation of the motor 28. This operation moves the jaw 12 forward, and clamps the tail portion 27 of the outer most funnel 15 with the end plate 14. Simultaneously, the jaw 12 activates the switch 30, which initiates the operation of the motor 29. This process moves the movable arm 13 to the extended position suspending a funnel 15 above the commode. After activating the switch 30 the jaw 12 stops. While extended out, the arm 13 pulls out the clamped outer most funnel 15 from a nested stack of funnels 15 loaded on the hub 23. Near the end plate 14, only one tail portion 27 (of the outer most funnel 15) remains exposed to be clamped. Because of the nested arrangement, the tail portion 27 of each funnel 15 in the stack is buried below the next funnel 15 stacked above it. Therefore, only one funnel 15 is pulled out at a time—when the user activates the sensor 16. The remaining funnels of the stack remain in place on the hub 23. The restraining arms 26 hold the protrusion 43 of the next funnel 15 in line to be dispensed (not shown in FIG. 5). In this process, the biasing device 25 (not shown in FIG. 5) pushes the hub 23 forward, which positions the tail portion 27 of the next forward most funnel 15 close to the end plate 14. On the next first activation, the process repeats. The jaw 12 can have a tapered thin leading edge to move under the raised tail portion 27 of the outer most funnel 15. The battery 35 or the electric plug 36 supplies the power.

Figure 6:
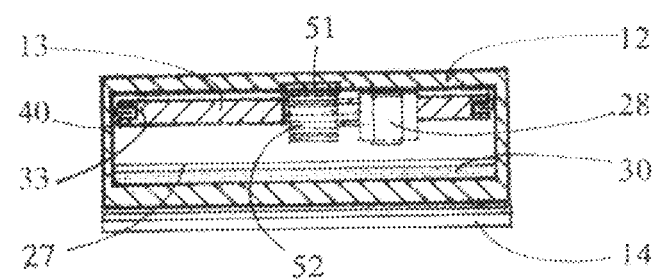
FIG. 6 shows a cross-sectional view of the movable arm, indicated by section lines 3-3 in FIG. 5.

FIG. 6 shows a cross-sectional view of the movable arm 13, indicated by section lines 3-3 in FIG. 5. Upon activation, the jaw 12 slides on the movable arm 13, forward on the first activation, and reverse on the second activation. A pair of tongues 40 and a pair of grooves 33 keep the reversible jaw 12 aligned and stay on the same plane even while moving. Different methods can be used for this purpose. The tongues 40 are located on both opposite inner sides of the jaw 12. The tongues 40 of the jaw 12 slide in the grooves 33, which are located on both outer sides of the arm 13. The rack 51 of the rack and pinion device is attached to the under surface of the top side of the reversible jaw 12. The pinion 52 is attached to the reversible motor 28. The motor 28 is mounted at the underside of the arm 13 and attaches to the rack 51 through an opening in the arm 13. The tail portion 27, the switch 30, and the end plate 14 are as previously discussed.

FIG. 7 shows a partial enlarged view of the operation from the dispensed and suspended position of the funnel 15, indicated by the dashed circle 7 in FIG. 3A (the dashed lines of FIG. 3A are shown in solid lines in FIG. 7). When the movable arm 13 is in the extended position, the user initiates a second activation of the sensor 16 after urinating. The sensor 16 initiates the operation of the motor 28 to move the jaw 12 out of the clamping position and allows the flushable funnel 15 in the suspended position to drop into the commode bowl 207. Immediately following, the jaw 12 activates the switch 31. The switch 31 initiates the operation of the motor 29, which moves the arm 13 to the stored position. The commode 200 is now free to function unimpeded (not shown in FIG. 7). When the arm 13 returns fully in the dispenser 11, the jaw 12 clears the tail portion 27 of the next outer most funnel 15 and allows the tail portion 27 to lift up (not shown in FIG. 7). On the next second activation, the process repeats. The activation device or sensor 16 is mounted on stop 38 but can be located anywhere on the apparatus 100 (not shown in FIG. 7). The end plate 14 is housing the switch 30.

FIG. 8 shows a detail of the front joint, indicated by the dashed circle 8 in FIG. 2. The joint is between the front left corner of the container 18R and the front right side of the dispenser 11 secured by a channel 41. The joint can be nailed, screwed, glued or attached by other suitable method. The commode cover 203 is visible in the FIG. 8.

FIG. 9 shows a detail of the rear joint, indicated by the dashed circle 9 in FIG. 2. The joint is between the rear left corner of the container 18R and the rear right side of the dispenser 11 secured by the channel 41. The joint can be nailed, screwed, glued or attached by other suitable method. The restraining arm 26 is anchored to the dispenser 11.

FIG. 10A shows a perspective view of the preferred embodiment of the flushable funnel 15 in a near horizontal orientation. The funnel 15 has a predetermined truncated cone shape, and is made of biodegradable materials. The materials can be compounds or papers having wet strength and water repellency while retaining the property of being flushable. The funnel 15 retains its strength and shape temporarily when wetted. Such papers can be manufactured. For example, an invention in U.S. Pat. No. 4,920,171 assigned to Monadnok papers Mills, Inc. (Bennington, N.H.) presented a paper product suitable for applications requiring wet strength and water repellency while retaining the property of being flushable. The invention in U.S. Pat. No. 4,920,171 can be used in its entirety for manufacturing the flushable funnels 15. The invention in U.S. Pat. No. 4,920,171 is directed to a coating composition for application to a flushable cellulosic based waterleaf sheet to impart transitory water repellency to at least one surface of the sheet. The composition comprises between about 20% by weight to about 70% by weight of relatively large particle size delaminated clay in combination with a polyethylene based polymer that has been produced by the drying of a colloidal polyethylene in water composition with the said clay. Being flushable, the funnel 15 paper have minimum wet strength resin, such as melamine formaldehyde, urea formaldehyde, or a neutral cure wet strength material. Furthermore, the funnel 15 is strong enough to withstand the force of a urine stream. The funnel 15 material can be made moderately slippery so that it can slide out easily from a stack of the funnels 15 stored around core 32 (not shown FIG. 10A). Each funnel 15 has two ends and a passage extending through between the ends. The funnel 15 is tapered so as to have a small end and a larger end.

FIG. 10A further shows the funnel 15 has a tail portion 27 attached on one side of the small open end. The funnel 15 has protrusion 43 all around the larger open end to allow for grip by the restraining arms 26 (not shown on FIG. 10A). The protrusion 43 cooperates with the restraining arms 26 and the biasing device 25 to dispense one funnel 15 at a time from the nested arrangement. The funnel 15 can be of different suitable shapes and sizes including, but not limited to square, round, oval, rectangular, or polygon. The funnel 15 can be made of suitable lengths to suit different sizes of commodes.

FIG. 10B shows another embodiment of the funnel 15 in a near horizontal orientation. In addition to the entire characteristic described in FIG. 10A including the tail portion 27 and the protrusion 43, the funnel 15 has fin portions 47 on the remaining sides of the small open end. The fin portions 47 on two sides can be used as handles and can be held by both hands while urinating; the portion 47 on the remaining side (close to the user) can act as a guard against dripping urine. This embodiment can be used with or without the apparatus 100. Without the apparatus 100 (not shown in FIG. 10B), the funnel 15 can be held in hands over the commode bowl. Then it can be dropped after the use, and can be flushed away.

FIG. 10C the funnel 15, arranged in a nested arrangement around the core 32. In addition to the entire characteristic described in FIG. 10A including the tail portion 27 forming a handle, the funnel 15 has a fin portion 47 on the opposite side of tail portion 27 forming another handle. The two handles can be held by a user above the commode bowl for urinating standing in the commode without the use of the apparatus 100 (not shown in the FIG. 10C). After the use, the user can drop the funnel 15 in the commode bowl. Then it can be flushed. The funnels 15 can be with or without the protrusion 43. This embodiment can be stored on top of the water tank or near the toilet. A single funnel 15 can be pulled out of the stack when needed. Since the bottom end is larger than the top end, the stack of funnels 15 stays stable at the stored position.

FIG. 11 shows a perspective view of the core 32, which can be made from cardboard or another suitable material and thickness. Its function is similar to the cardboard core of toilet paper rolls. The core 32 has a flange 44 for pulling it out from the hub 23 (not shown in FIG. 11). The core 32 can be disposable or refillable.

Figure 12:
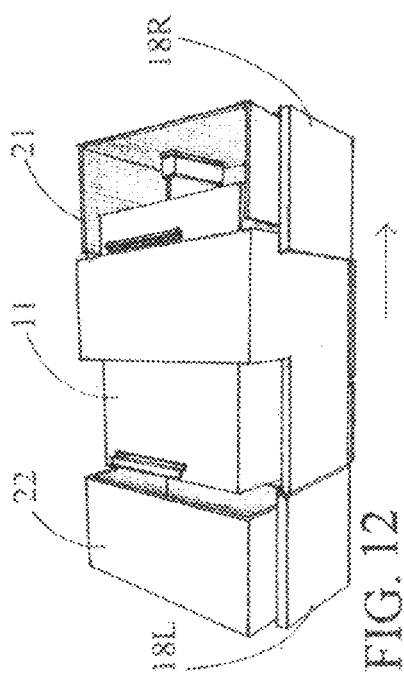
FIG. 12 shows a packaged version of the preferred embodiment.

FIG. 12 shows a compact packing version of the apparatus 100 to save space and cost. The drawer 21 is slightly open showing that the dispenser 11 can be placed inside the drawer 21. A side of the containers 18L and 18R adjacent to the dispenser 11 is precut leaving a small slit on either end of that side. These slits fit into grove of the channels 41 (not shown in FIG. 12) attaching the containers 18L and 18R to the dispenser 11. With these precut sides the containers 18L and 18R can be wrapped around the storage section 22 as shown. Thus, the packing can be made smaller. The packing version occupies less space than the assembled one and may cost less than the assembled one. A consumer can easily assemble it.

Figure 13:
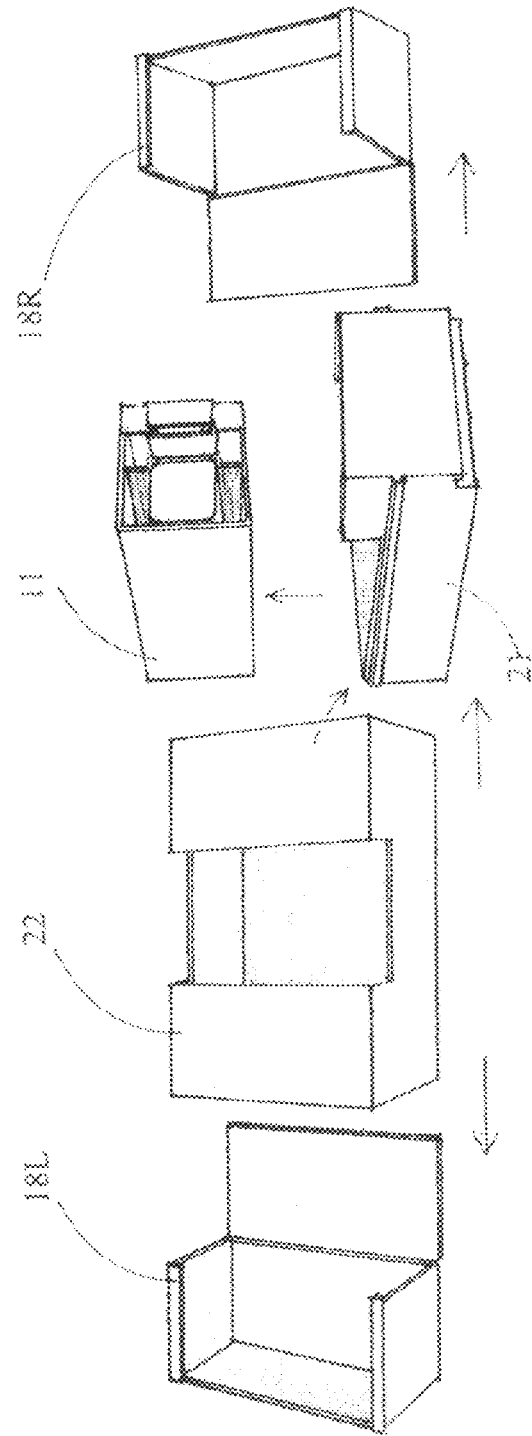
FIG. 13 shows an unpacked version of the preferred embodiment.

FIG. 13 shows how to unpack different components of the urinal apparatus. First, separate the container 18L and the container 18R from both ends. Then slide out the drawer 21 from the storage section 22. Take out the dispenser 11 from the drawer 21. Thus, the apparatus can be made ready to be assembled.

Figure 14:
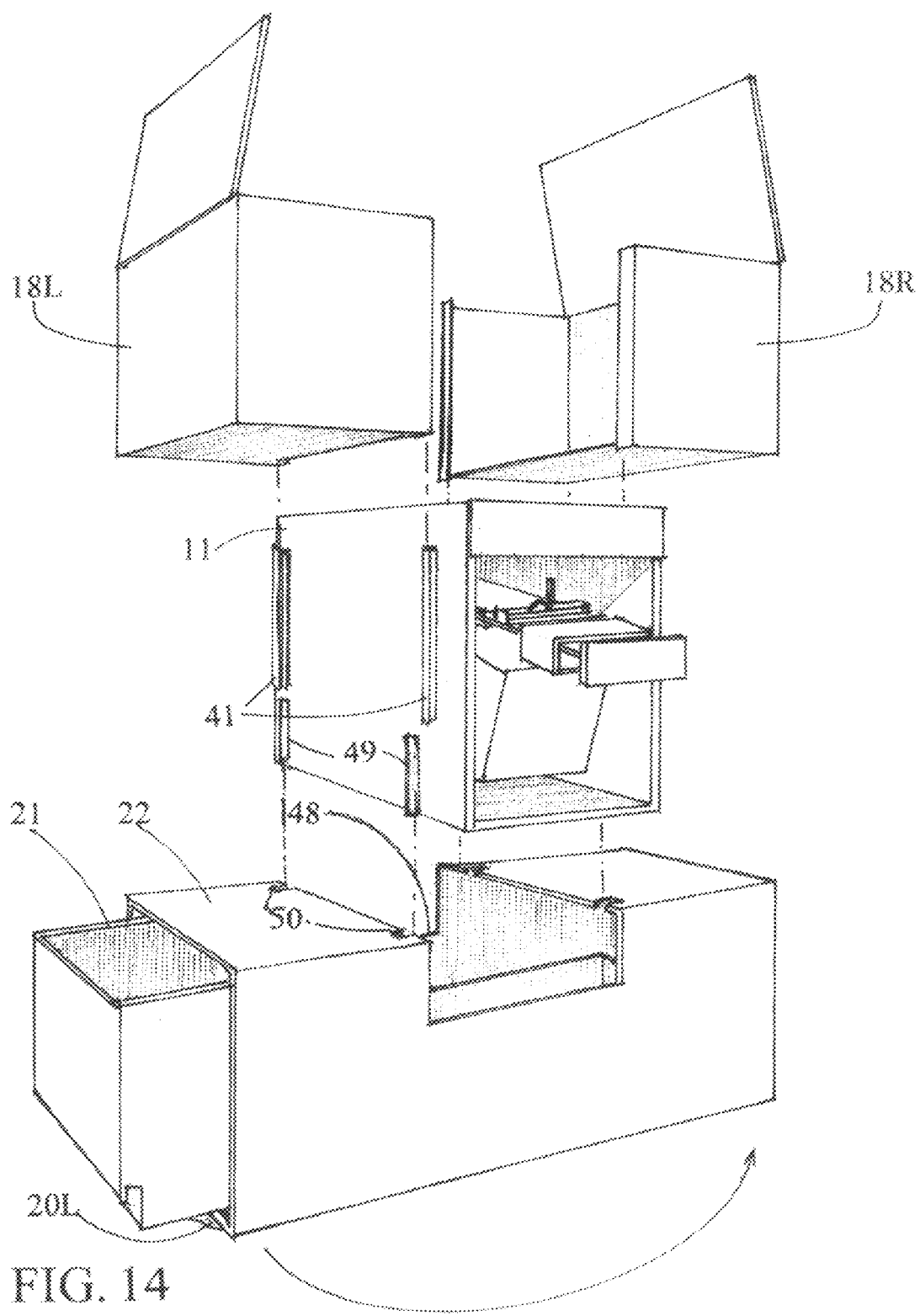
FIG. 14 shows an assembly diagram of the preferred embodiment.

FIG. 14 shows an assembly diagram of the urinal apparatus for a commode. First, place and push the storage section 22 slightly on the top surface of the water tank 205 (not shown in FIG. 14). The fastening device 20L and 20R (not shown in FIG. 14) attaches the apparatus on the water tank 205 (not shown in FIG. 14). The storage section 22 can be positioned to access the drawer 21 from the left or right side. Next, the dispenser 11 slides and fits on a notch 48 located on the storage section 22. Bands 49 slide in sears 50, which lock in the dispenser 11 with the storage section 22. Then, slide the containers 18L and 18R in the groove formed by channels 41. This compact version is just one example, and can be made in several different ways. Thus, a consumer can easily assemble the apparatus in a short time.

ADVANTAGES

The power-operated urinal apparatus for a commode alleviates deficiencies of prior arts in the same field and provides further benefits including:

(a) Prevents urine spills around the commode.
(b) Reduces splashing and embarrassing sounds of urine stream.
(c) Requires no additional floor space.
(d) Requires no additional plumbing work.
(e) Installs easily by a layperson in a short time.
(f) Has a storage space for extra flushable funnels and toilet paper rolls.
(g) Is hygienic, economical, novel, unique, useful and pleasing.

CONCLUSION, RAMIFICATIONS, AND SCOPE

Thus, at least one embodiment of the urinal apparatus for a commode provides a more reliable, clean, and economical apparatus that can be used by a wide range of people. Said apparatus facilitates urinal function without installing a traditional urinal and extra plumbing. Said apparatus is easy to install and is aesthetically pleasing than a urinal and can work better than the prior art. As an added bonus, said apparatus stores extra bio-degradable funnels and toilet papers.

The elements described here can be duplicated or eliminated, changed in size and made in different shapes and colors. They can be connected or associated with adjacent elements in a different manner. They can be made integrally or separately, i.e. modular or in sections.

While my above description contains much specificity, these should not be construed as limitations on the scope, but rather as an exemplification of one preferred embodiment thereof. Accordingly, the scope should be determined not by the embodiments illustrated, but by the appended claims and their legal equivalent.

I claim:

1. A power-operated urinal apparatus to be used with a toilet, the toilet having an aperture for receiving human waste, comprising:
   a. a supply of flushable funnels, each flushable funnel having a top open end and a bottom open end, and a passage between said two ends;
   b. a power-driven dispenser activated by a user, said dispenser being movable under power from a stored position where the dispenser allows unimpeded use of the aperture, and an extended position where the dispenser locates and holds one of said flushable funnels in a suspended position with the top end of the flushable funnel above the aperture and the bottom end of the flushable funnel located relative to the aperture to direct fluids from said flushable funnel into the aperture without requiring any contact between the user and said apparatus during the use of said apparatus;
   c. said power-driven dispenser further being operable to move said power-driven dispenser under power to cause said dispenser to release said flushable funnel into the toilet and to move said dispenser from said extended position to said stored position, without requiring any contact between the user and said apparatus during use of said apparatus.

2. The urinal apparatus of claim 1, wherein said flushable funnels in the supply of flushable funnels are at a first orientation and the flushable funnel in the suspended position is at a second orientation that is different from the first orientation.

3. The urinal apparatus of claim 1, wherein said flushable funnels are made of water-flushable materials tough enough to withstand fluids, slightly slippery, and have transitory water repellency.

4. The urinal apparatus of claim 1, wherein said power-driven dispenser further comprises a power-driven movable arm, said movable arm is supported by a sleeve for enabling said movable arm to move between the stored position and the extended position.

5. The urinal apparatus to be used with a toilet as in claim 4, wherein said sleeve is pivotally supported with aid of a track device for enabling said sleeve to move up and down, and having a means for holding said sleeve up to facilitate reloading a plurality of said flushable funnels to said supply of flushable funnels.

6. The urinal apparatus to be used with a toilet as in claim 4, wherein said movable arm includes a means for height adjusting for a user to adjust a height of the top end of said flushable funnel in the suspended position suitable to said user.

7. The urinal apparatus to be used with a toilet as in claim 4, wherein said movable arm is moved between the stored position and the extended position by a rack and pinion device, said rack and pinion device is connected to a first motor.

8. The urinal apparatus to be used with a toilet as in claim 4, further comprising an end plate and a stop on said power-driven movable arm and a movable jaw that moves on said movable arm between said end plate and said stop, said end plate and said jaw releasably clamping a portion of one of the flushable funnels.

9. The urinal apparatus to be used with a toilet as in claim 8, further comprising a sensor for activation by a human user of the aperture, said sensor initiating the operation of a second motor that moves said jaw to a clamping position with said end plate before said first motor is initiated to extend said movable arm to the extended position.

10. The urinal apparatus to be used with a toilet as in claim 1, wherein the supply of flushable funnels comprises a nested arrangement;
wherein each of said flushable funnels includes a tail portion at the top end to be clamped.

11. The urinal apparatus of claim 9, wherein said sensor activation is a first activation, said sensor having a second activation by a human user when said movable arm is in the extended position, wherein said sensor initiates the operation of the second motor to move the jaw out of the clamping position and allows the flushable funnel in the suspended position to drop into the aperture.

12. The urinal apparatus of claim 9 wherein upon said second activation of said sensor and after said second motor moves the jaw out of the clamping position, said first motor moves said movable arm to the stored position.

13. The urinal apparatus of claim 1, wherein said supply of flushable funnels comprises a nested arrangement, each flushable funnel is tapered from the top end to the bottom end.

14. The urinal apparatus to be used with a toilet as in claim 1, wherein said power-driven dispenser comprises a movable arm;
wherein said supply of flushable funnels includes a biasing device to urge said flushable funnels towards an end of said movable arm.

15. The urinal apparatus to be used with a toilet as in claim 1, wherein said supply of flushable funnels includes a hub to support a plurality of said flushable funnels.

16. The urinal apparatus to be used with a toilet as in claim 1, wherein said supply of flushable funnels includes restraining arms with a portion extending inwards.

17. The urinal apparatus to be used with a toilet in claim 1, further comprising a protrusion adjacent the bottom end of said flushable funnels to cooperate with the restraining arms to dispense said flushable funnels from the nested arrangement one at a time.

18. The urinal apparatus to be used with a toilet as in claim 1, wherein said flushable funnel includes a flap portion around at least a portion of the top end forming a handle.

19. The urinal apparatus to be used with a toilet as in claim 1, wherein said apparatus includes storage space to store extra supplies of said flushable funnels.

20. The urinal apparatus to be used with a toilet as in claim 1, wherein said apparatus includes storage space to store toilet paper.

21. The urinal apparatus to be used with a toilet as in claim 1, wherein said apparatus can be made in separate sections adapted to reduce its packing size.

22. The urinal apparatus to be used with a toilet as in claim 1, wherein the toilet aperture receives human waste.

23. The urinal apparatus to be used with a toilet as in claim 1, wherein said urinal apparatus having at least one means for fastening on an exterior of said urinal apparatus for mounting said urinal apparatus to an object or a water tank of a toilet.

* * * * *